United States Patent
Han et al.

(10) Patent No.: US 9,644,020 B2
(45) Date of Patent: May 9, 2017

(54) HUMAN TIM-3 FUSION PROTEIN CAPABLE OF BLOCKING TIM-3 SIGNALING PATHWAY

(71) Applicant: Institute of Basic Medical Science, the Academy of Military Medical Science of the Chinese PLA, Beijing (CN)

(72) Inventors: Gencheng Han, Beijing (CN); Guojiang Chen, Beijing (CN); Xingwei Jiang, Beijing (CN); Renxi Wang, Beijing (CN); He Xiao, Beijing (CN); Chunmei Hou, Beijing (CN); Jiahui Yu, Beijing (CN); Zhi Zhao, Beijing (CN); Jiannan Feng, Beijing (CN); Yan Li, Beijing (CN); Beifen Shen, Beijing (CN)

(73) Assignee: Institute of Basic Medical Science, the Academy of Military Medical Science of the Chinese PLA (CN)

( * ) Notice: Subject to any disclaimer, the term of this patent is extended or adjusted under 35 U.S.C. 154(b) by 0 days.

(21) Appl. No.: 15/114,140

(22) PCT Filed: Jan. 20, 2015

(86) PCT No.: PCT/CN2015/000031
§ 371 (c)(1),
(2) Date: Oct. 7, 2016

(87) PCT Pub. No.: WO2015/109931
PCT Pub. Date: Jul. 30, 2015

(65) Prior Publication Data
US 2017/0029485 A1    Feb. 2, 2017

(30) Foreign Application Priority Data
Jan. 26, 2014    (CN) .......................... 2014 1 0036782

(51) Int. Cl.
| | | |
|---|---|---|
| A61K 6/00 | (2006.01) |
| A61K 31/00 | (2006.01) |
| A61K 31/70 | (2006.01) |
| A61K 31/7028 | (2006.01) |
| A61K 31/7034 | (2006.01) |
| A61K 31/704 | (2006.01) |
| A61K 31/7042 | (2006.01) |
| A61K 31/7048 | (2006.01) |
| A61K 31/7076 | (2006.01) |
| C07K 14/705 | (2006.01) |
| C07K 16/00 | (2006.01) |
| C07K 19/00 | (2006.01) |
| A61K 47/26 | (2006.01) |
| A61K 47/02 | (2006.01) |
| A61K 48/00 | (2006.01) |
| A61K 39/00 | (2006.01) |
| A61K 38/00 | (2006.01) |

(52) U.S. Cl.
CPC ........ *C07K 14/70503* (2013.01); *A61K 47/02* (2013.01); *A61K 47/26* (2013.01); *C07K 16/00* (2013.01); *C07K 19/00* (2013.01); *A61K 38/00* (2013.01); *A61K 48/00* (2013.01); *A61K 2039/505* (2013.01); *C07K 2317/76* (2013.01); *C07K 2319/00* (2013.01)

(58) Field of Classification Search
None
See application file for complete search history.

(56) References Cited

U.S. PATENT DOCUMENTS

2005/0276756 A1    12/2005    Hoo et al.

FOREIGN PATENT DOCUMENTS

CN          101035561 A    9/2007

OTHER PUBLICATIONS

International Search Report for PCT/CN2015/000031 mailed Apr. 27, 2015.

*Primary Examiner* — Alana Harris Dent
(74) *Attorney, Agent, or Firm* — Drinker Biddle & Reath LLP (57) ABSTRACT

The present invention provides a human Tim-3-Ig fusion protein which can block Tim-3 signal pathway, and said Ig fusion protein comprises Tim-3 protein, human Ig fragment, and the linking sequence therebetween. In the present invention, a human Tim-3-Ig gene is obtained by an artificial synthesis process; an expression vector containing the Tim-3-Ig gene is constructed; and the prepared Ig fusion protein is tested in an expression verification experiment, a binding activity experiment, a blocking activity experiment in different cell lines, and in vivo experiments in mice. The human Tim-3-Ig fusion protein prepared in the present invention can be used to treat immunological diseases caused by high expression of Tim-3.

5 Claims, 3 Drawing Sheets

SEQUENCE LISTING

```
<160> NUMBER OF SEQ ID NOS: 6

<210> SEQ ID NO 1
<211> LENGTH: 440
<212> TYPE: PRT
<213> ORGANISM: Artificial sequence
<220> FEATURE:
<223> OTHER INFORMATION: Tim-3-Ig fusion protein

<400> SEQUENCE: 1

Met Gly Ser Ser His His His His His Ser Ser Gly Leu Val Pro
1               5                   10                  15

Arg Gly Ser His Met Ser Glu Val Glu Tyr Arg Ala Glu Val Gly Gln
            20                  25                  30

Asn Ala Tyr Leu Pro Cys Phe Tyr Thr Pro Ala Ala Pro Gly Asn Leu
            35                  40                  45

Val Pro Val Cys Trp Gly Lys Gly Ala Cys Pro Val Phe Glu Cys Gly
        50                  55                  60

Asn Val Val Leu Arg Thr Asp Glu Arg Asp Val Asn Tyr Trp Thr Ser
65                  70                  75                  80

Arg Tyr Trp Leu Asn Gly Asp Phe Arg Lys Gly Asp Val Ser Leu Thr
                85                  90                  95

Ile Glu Asn Val Thr Leu Ala Asp Ser Gly Ile Tyr Cys Cys Arg Ile
                100                 105                 110

Gln Ile Pro Gly Ile Met Asn Asp Glu Lys Phe Asn Leu Lys Leu Val
            115                 120                 125

Ile Lys Pro Ala Lys Val Thr Pro Ala Pro Thr Leu Gln Arg Asp Phe
        130                 135                 140

Thr Ala Ala Phe Pro Arg Met Leu Thr Thr Arg Gly His Gly Pro Ala
145                 150                 155                 160

Glu Thr Gln Thr Leu Gly Ser Leu Pro Asp Ile Asn Leu Thr Gln Ile
                165                 170                 175

Ser Thr Leu Ala Asn Glu Leu Arg Asp Ser Arg Leu Ala Asn Asp Leu
                180                 185                 190

Arg Asp Ser Gly Ala Thr Ile Arg Ile Gly Ala Ser Met Thr Gly Gly
            195                 200                 205

Gln Gln Met Gly Arg Gly Ser Gly Gly Gly Ser Gly Gly Gly Gly
        210                 215                 220

Ser Gly Gly Gly Ser Pro Ser Val Phe Leu Phe Pro Pro Lys Pro
225                 230                 235                 240

Lys Asp Thr Leu Met Ile Ser Arg Thr Pro Glu Val Thr Cys Val Val
                245                 250                 255

Val Asp Val Ser His Glu Asp Pro Glu Val Lys Phe Asn Trp Tyr Val
                260                 265                 270

Asp Gly Val Glu Val His Asn Ala Lys Thr Lys Pro Arg Glu Glu Gln
            275                 280                 285

Tyr Asn Ser Thr Tyr Arg Val Val Ser Val Leu Thr Val Leu His Gln
        290                 295                 300

Asp Trp Leu Asn Gly Lys Glu Tyr Lys Cys Lys Val Ser Asn Lys Ala
305                 310                 315                 320
```

| | | | | | | | | | | | |
|---|---|---|---|---|---|---|---|---|---|---|---|
|Leu|Pro|Ala|Pro|Ile|Glu|Lys|Thr|Ile|Ser|Lys|Ala|Lys|Gly|Gln|Pro|
| | | | |325| | | |330| | | |335| | | |

Leu Pro Ala Pro Ile Glu Lys Thr Ile Ser Lys Ala Lys Gly Gln Pro
            325                 330                 335

Arg Glu Pro Gln Val Tyr Thr Leu Pro Pro Ser Arg Glu Glu Met Thr
        340                 345                 350

Lys Asn Gln Val Ser Leu Thr Cys Leu Val Lys Gly Phe Tyr Pro Ser
        355                 360                 365

Asp Ile Ala Val Glu Trp Glu Ser Asn Gly Gln Pro Glu Asn Asn Tyr
        370                 375                 380

Lys Thr Thr Pro Pro Val Leu Asp Ser Asp Gly Ser Phe Phe Leu Tyr
385                 390                 395                 400

Ser Lys Leu Thr Val Asp Lys Ser Arg Trp Gln Gln Gly Asn Val Phe
            405                 410                 415

Ser Cys Ser Val Met His Glu Ala Leu His Asn His Tyr Thr Gln Lys
            420                 425                 430

Ser Leu Ser Leu Ser Pro Gly Lys
            435                 440

```
<210> SEQ ID NO 2
<211> LENGTH: 1323
<212> TYPE: DNA
<213> ORGANISM: Artificial sequence
<220> FEATURE:
<223> OTHER INFORMATION: Tim-3-Ig fusion protein coding sequence

<400> SEQUENCE: 2
atgggcagca gccatcatca tcatcatcac agcagcggcc tggtgccgcg cggcagccat      60
atgtcagaag tggaatacag agcggaggtc ggtcagaatg cctatctgcc ctgcttctac     120
accccagccg ccccagggaa cctcgtgccc gtctgctggg caaaggagc ctgtcctgtg     180
tttgaatgtg caacgtggt gctcaggact gatgaaaggg atgtgaatta ttggacatcc     240
agatactggc taaatgggga tttccgcaaa ggagatgtgt ccctgaccat agagaatgtg     300
actctagcag acagtgggat ctactgctgc cggatccaaa tcccaggcat aatgaatgat     360
gaaaaattta acctgaagtt ggtcatcaaa ccagccaagg tcacccctgc accgactctg     420
cagagagact tcactgcagc ctttccaagg atgcttacca ccaggggaca tggcccagca     480
gagacacaga cactggggag cctccctgat ataaatctaa cacaaatatc cacattggcc     540
aatgagttac gggactctag attggccaat gacttacggg actctggagc aaccatcaga     600
ataggcgcta gcatgactgg tggacagcaa atgggtcgcg gatccggtgg cggtggctcg     660
ggcggtggtg ggtcgggtgg cggcggatct ccgtcagtct tcctcttccc cccaaaaccc     720
aaggacaccc tcatgatctc ccggaccccct gaggtcacat gcgtggtggt ggacgtgagc     780
cacgaagacc ctgaggtcaa gttcaactgg tacgtggacg gcgtggaggt gcataatgcc     840
aagacaaagc cgcgggagga gcagtacaac agcacgtacc gtgtggtcag cgtcctcacc     900
gtcctgcacc aggactggct gaatggcaag gagtacaagt gcaaggtctc caacaaagcc     960
ctcccagccc ccatcgagaa aaccatctcc aaagccaaag ggcagccccg agaaccacag    1020
gtgtacaccc tgcccccatc ccgggaggag atgaccaaga accaggtcag cctgacctgc    1080
ctggtcaaag gcttctatcc cagcgacatc gccgtggagt gggagagcaa tgggcagccg    1140
gagaacaact acaagaccac gcctcccgtg ctggactccg acggctcctt cttcctctat    1200
agcaagctca ccgtggacaa gagcaggtgg cagcagggga acgtcttctc atgctccgtg    1260
atgcatgagg ctctgcacaa ccactacacg cagaagagcc tctccctgtc tccgggtaaa    1320
taa                                                                   1323
```

<210> SEQ ID NO 3
<211> LENGTH: 1680
<212> TYPE: DNA
<213> ORGANISM: Artificial sequence
<220> FEATURE:
<223> OTHER INFORMATION: Coding sequence for Control 1 (D1 protein)

<400> SEQUENCE: 3

```
atgggcagca gccatcatca tcatcatcac agcagcggcc tggtgccgcg cggcagccat      60
atgtcagaag tggaatacag agcggaggtc ggtcagaatg cctatctgcc ctgcttctac     120
accccagccg ccccagggaa cctcgtgccc gtctgctggg gcaaaggagc ctgtcctgtg     180
tttgaatgtg gcaacgtggt gctcaggact gatgaaaggg atgtgaatta ttggacatcc     240
agatactggc taaatgggga tttccgcaaa ggagatgtgt ccctgaccat agagaatgtg     300
actctagcag acagtgggat ctactgctgc cggatccaaa tcccaggcat aatgaatgat     360
gaaaaattta acctgaagtt ggtcatcaaa ccagccaagg tcacccctgc accgactctg     420
cagagagact tcactgcagc ctttccaagg atgcttacca ccaggggaca tggcccagca     480
gagacacaga cactggggag cctccctgat ataaatctaa cacaaatatc cacattggcc     540
aatgagttac gggactctag attggccaat gacttacggg actctggagc aaccatcaga     600
ataggcgcta gcatgactgg tggacagcaa atgggtcgcg gatccggtgg cggtggctcg     660
ggcggtggtg ggtcgggtgg cggcggatct tccaccaagg gcccatcggt cttccccctg     720
gcaccctcct ccaagagcac ctctgggggc acagcggccc tgggctgcct ggtcaaggac     780
tacttccccg aaccggtgac ggtgtcgtgg aactcaggcg ccctgaccag cggcgtgcac     840
accttcccgg ctgtcctaca gtcctcagga ctctactccc tcagcagcgt ggtgaccgtg     900
ccctccagca gcttgggcac ccagacctac atctgcaacg tgaatcacaa gcccagcaac     960
accaaggtgg acaagagagt tgagcccaaa tcttgtgaca aaactcacac atgcccaccg    1020
tgcccagcac ctgaactcct ggggggaccg tcagtcttcc tcttcccccc aaaacccaag    1080
gacaccctca tgatctcccg gacccctgag gtcacatgcg tggtggtgga cgtgagccac    1140
gaagaccctg aggtcaagtt caactggtac gtggacggcg tggaggtgca taatgccaag    1200
acaaagccgc gggaggagca gtacaacagc acgtaccgtg tggtcagcgt cctcaccgtc    1260
ctgcaccagg actggctgaa tggcaaggag tacaagtgca aggtctccaa caaagccctc    1320
ccagccccca tcgagaaaac catctccaaa gccaaagggc agccccgaga accacaggtg    1380
tacaccctgc ccccatcccg ggaggagatg accaagaacc aggtcagcct gacctgcctg    1440
gtcaaaggct tctatcccag cgacatcgcc gtggagtggg agagcaatgg gcagccggag    1500
aacaactaca agaccacgcc tcccgtgctg gactccgacg gctccttctt cctctatagc    1560
aagctcaccg tggacaagag caggtggcag caggggaacg tcttctcatg ctccgtgatg    1620
catgaggctc tgcacaacca ctacacgcag aagagcctct ccctgtcccc gggtaaatga    1680
```

<210> SEQ ID NO 4
<211> LENGTH: 1386
<212> TYPE: DNA
<213> ORGANISM: Artificial sequence
<220> FEATURE:
<223> OTHER INFORMATION: Coding sequence for Control 2 (D2 protein)

<400> SEQUENCE: 4

```
atgggcagca gccatcatca tcatcatcac agcagcggcc tggtgccgcg cggcagccat      60
```

-continued

| | |
|---|---|
| atgtcagaag tggaatacag agcggaggtc ggtcagaatg cctatctgcc ctgcttctac | 120 |
| accccagccg ccccagggaa cctcgtgccc gtctgctggg gcaaaggagc ctgtcctgtg | 180 |
| tttgaatgtg gcaacgtggt gctcaggact gatgaaaggg atgtgaatta ttggacatcc | 240 |
| agatactggc taaatgggga tttccgcaaa ggagatgtgt ccctgaccat agagaatgtg | 300 |
| actctagcag acagtgggat ctactgctgc cggatccaaa tcccaggcat aatgaatgat | 360 |
| gaaaaattta acctgaagtt ggtcatcaaa ccagccaagg tcacccctgc accgactctg | 420 |
| cagagagact tcactgcagc ctttccaagg atgcttacca ccagggggaca tggcccagca | 480 |
| gagacacaga cactggggag cctccctgat ataaatctaa cacaaatatc cacattggcc | 540 |
| aatgagttac gggactctag attggccaat gacttacggg actctggagc aaccatcaga | 600 |
| ataggcgcta gcatgactgg tggacagcaa atgggtcgcg gatccggtgg cggtggctcg | 660 |
| ggcggtggtg ggtcgggtgg cggcggatct cccaaatctt gtgacaaaac tcacacatgc | 720 |
| ccaccgtgcc cagcacctga actcctgggg ggaccgtcag tcttcctctt ccccccaaaa | 780 |
| cccaaggaca ccctcatgat ctcccggacc cctgaggtca catgcgtggt ggtggacgtg | 840 |
| agccacgaag accctgaggt caagttcaac tggtacgtgg acggcgtgga ggtgcataat | 900 |
| gccaagacaa agccgcggga ggagcagtac aacagcacgt accgtgtggt cagcgtcctc | 960 |
| accgtcctgc accaggactg gctgaatggc aaggagtaca agtgcaaggt ctccaacaaa | 1020 |
| gccctcccag cccccatcga gaaaaccatc tccaaagcca aagggcagcc ccgagaacca | 1080 |
| caggtgtaca ccctgccccc atcccgggag gagatgacca agaaccaggt cagcctgacc | 1140 |
| tgcctggtca aaggcttcta tcccagcgac atcgccgtgg agtgggagag caatgggcag | 1200 |
| ccggagaaca actacaagac cacgcctccc gtgctggact ccgacggctc cttcttcctc | 1260 |
| tatagcaagc tcaccgtgga caagagcagg tggcagcagg ggaacgtctt ctcatgctcc | 1320 |
| gtgatgcatg aggctctgca caaccactac acgcagaaga gcctctccct gtccccgggt | 1380 |
| aaatga | 1386 |

<210> SEQ ID NO 5
<211> LENGTH: 1323
<212> TYPE: DNA
<213> ORGANISM: Artificial sequence
<220> FEATURE:
<223> OTHER INFORMATION: Coding sequence for Control 3 (D3 protein)

<400> SEQUENCE: 5

| | |
|---|---|
| atgggcagca gccatcatca tcatcatcac agcagcggcc tggtgccgcg cggcagccat | 60 |
| atggaatgtg gcaacgtggt gctcaggact gatgaaaggg atgtgaatta ttggacatcc | 120 |
| agatactggc taaatgggga tttccgcaaa ggagatgtgt ccctgaccat agagaatgtg | 180 |
| actctagcag acagtgggat ctactgctgc cggatccaaa tcccaggcat aatgaatgat | 240 |
| gaaaaattta acctgaagtt ggtcatcaaa ccagccaagg tcacccctgc accgactctg | 300 |
| cagagagact tcactgcagc ctttccaagg atgcttacca ccagggggaca tggcccagca | 360 |
| gagacacaga cactggggag cctccctgat ataaatctaa cacaaatatc cacattggcc | 420 |
| aatgagttac gggactctag attggccaat gacttacggg actctggagc aaccatcaga | 480 |
| ataggcatct acatcggagc agggatctgt gctgggctgg ctctggctct tatcttcggc | 540 |
| gctttaattt tcaaatggta ttctcatagc aaagagaaga tacagaattt aagcctcatc | 600 |
| tctttggcta gcatgactgg tggacagcaa atgggtcgcg gatccggtgg cggtggctcg | 660 |
| ggcggtggtg ggtcgggtgg cggcggatct ccgtcagtct tcctcttccc cccaaaaccc | 720 |

```
aaggacaccc tcatgatctc ccggaccct gaggtcacat gcgtggtggt ggacgtgagc      780
cacgaagacc ctgaggtcaa gttcaactgg tacgtggacg gcgtggaggt gcataatgcc      840
aagacaaagc cgcgggagga gcagtacaac agcacgtacc gtgtggtcag cgtcctcacc      900
gtcctgcacc aggactggct gaatggcaag gagtacaagt gcaaggtctc caacaaagcc      960
ctcccagccc ccatcgagaa aaccatctcc aaagccaaag gcagccccg agaaccacag      1020 gtgtacaccc tgcccccatc ccgggaggag atgaccaaga accaggtcag cctgacctgc      1080
ctggtcaaag gcttctatcc cagcgacatc gccgtggagt gggagagcaa tgggcagccg      1140
gagaacaact acaagaccac gcctcccgtg ctggactccg acggctcctt cttcctctat      1200
agcaagctca ccgtggacaa gagcaggtgg cagcagggga acgtcttctc atgctccgtg      1260
atgcatgagg ctctgcacaa ccactacacg cagaagagcc tctccctgtc tccgggtaaa      1320
taa                                                                    1323
```

<210> SEQ ID NO 6
<211> LENGTH: 1323
<212> TYPE: DNA
<213> ORGANISM: Artificial sequence
<220> FEATURE:
<223> OTHER INFORMATION: Coding sequence for Control 4 (D4 protein)

<400> SEQUENCE: 6

```
atgggcagca gccatcatca tcatcatcac agcagcggcc tggtgccgcg cggcagccat      60
atgctagcag acagtgggat ctactgctgc cggatccaaa tcccaggcat aatgaatgat     120
gaaaaattta acctgaagtt ggtcatcaaa ccagccaagg tcacccctgc accgactctg     180
cagagagact tcactgcagc ctttccaagg atgcttacca ccaggggaca tggcccagca     240
gagacacaga cactggggag cctccctgat ataaatctaa cacaaatatc cacattggcc     300
aatgagttac gggactctag attggccaat gacttacggg actctggagc aaccatcaga     360
ataggcatct acatcggagc agggatctgt gctgggctgg ctctggctct tatcttcggc     420
gctttaattt tcaaatggta ttctcatagc aaagagaaga tacagaattt aagcctcatc     480
tctttggcca acctccctcc ctcaggattg gcaaatgcag tagcagaggg aattcgctca     540
gaagaaaaca tctataccat tgaagagaac gtatatgaag tggaggagcc caatgagtat     600
tattgcgcta gcatgactgg tggacagcaa atgggtcgcg gatccggtgg cggtggctcg     660
ggcggtggtg ggtcgggtgg cggcggatct ccgtcagtct tcctcttccc cccaaaaccc     720
aaggacaccc tcatgatctc ccggaccct gaggtcacat gcgtggtggt ggacgtgagc      780
cacgaagacc ctgaggtcaa gttcaactgg tacgtggacg gcgtggaggt gcataatgcc      840
aagacaaagc cgcgggagga gcagtacaac agcacgtacc gtgtggtcag cgtcctcacc      900
gtcctgcacc aggactggct gaatggcaag gagtacaagt gcaaggtctc caacaaagcc      960
ctcccagccc ccatcgagaa aaccatctcc aaagccaaag gcagccccg agaaccacag      1020 gtgtacaccc tgcccccatc ccgggaggag atgaccaaga accaggtcag cctgacctgc      1080
ctggtcaaag gcttctatcc cagcgacatc gccgtggagt gggagagcaa tgggcagccg      1140
gagaacaact acaagaccac gcctcccgtg ctggactccg acggctcctt cttcctctat      1200
agcaagctca ccgtggacaa gagcaggtgg cagcagggga acgtcttctc atgctccgtg      1260
atgcatgagg ctctgcacaa ccactacacg cagaagagcc tctccctgtc tccgggtaaa      1320
taa                                                                    1323
```

HUMAN TIM-3 FUSION PROTEIN CAPABLE OF BLOCKING TIM-3 SIGNALING PATHWAY

RELATED APPLICATIONS

This application is a national stage application (under 35 U.S.C. §371) of PCT/CN2015/000031, filed Jan. 20, 2015, which claims benefit of Chinese Application No. 201410036782.4, filed Jan. 26, 2014.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence_Listing_215983_0001. The size of the text file is 15 KB, and the text file was created on Oct. 6, 2016.

TECHNICAL FIELD

The present invention relates to a fusion protein, and specifically to a human Tim-3-Ig fusion protein and a preparation containing thereof. The present invention also relates to use of the human Tim-3-Ig fusion protein for treating immunological diseases.

BACKGROUND OF THE INVENTION

Tim-3 is a member of the T-cell immunoglobulin domain and Mucin domain protein (Tim) family in structure. Tim family is widely involved in immunoregulation processes of the body, and thus people paid more attention to the function of this family. Tim-3 is specifically expressed on the surface of activated Th1 and Th17 effector cells, but not on Th2 cells. It is known in the art that Galectin-9 (Gal-9) is the natural ligand for Tim-3, and this molecule is widely expressed in peripheral immune system. After Tim-3 and Gal-9 are combined, a series of signal pathways can be activated so as to inhibit the activation of immunocytes, including T-cells and innate immunocytes such as macrophage etc. It was indicated in some studies that the high expression of Tim-3 on immunocytes is closely related to the immune dysfunction in patients with tumor and chronic viral infection. It was also indicated that such means capable of blocking the combination of Tim-3 and Gal-9 can prevent the Th1 and Th17 cells from dying, enhance the activities of T-effector cells, and recover the immune functions.

In one aspect, in some autoimmune diseases like systemic lupus erythematosus (SLE) and asthma etc., the increased expression of Gal-9 or Tim-3 will inhibit the functions of Th1 cells, which in turn breaks the immunologic balance of the body, and results in the increased activity of pathological Th2 cells and therefore onset of diseases. Under the circumstances, such means capable of blocking the combination of Tim-3/Gal-9 can promote the recovery of immunologic balance of the body and alleviate the progression of diseases. In another aspect, in some autoimmune diseases like inflammatory bowel disease and type I diabetes mellitus, some studies showed that blocking the activities of Tim-3 can enhance the functions of Th1 effector cells in the body, which further increases the autoimmune damages. The results also indicate that Tim-3 plays an important role in maintaining the immunologic balance of the body.

It is shown in the above studies that Tim-3 pathway has important immune regulatory functions, and abnormal expression of Tim-3 is closely related to the onsets and progressions of many kinds of diseases. However, there is no blocking agent for Tim-3 signal pathway with good effects so far. Accordingly, to better study the pathogenesis of some diseases and improve the diagnosis and treatment thereof, it is important to develop a blocking agent for Tim-3 signal pathway with high specificity and good blocking effect.

SUMMARY OF THE INVENTION

In order to solve the above problems, the present invention discloses a Tim-3-Ig fusion protein which has good blocking effect on Tim-3 signal pathway.

The increased molecular weight of the molecule for modifying Tim-3 will influence the correct combination between Tim-3 and its ligand, which therefore will influence the biological activities of Tim-3. The present invention provides a Tim-3-Ig fusion protein, wherein said Tim-3 is a Tim-3 fragment preferably selected from the full length sequence of Tim-3, and said Ig is an Ig fragment preferably selected from the Fc sequence of IgG. This Tim-3-Ig fusion protein has increased biological activities, decreased cost, and a higher practical value.

The present invention is related to a protein medicament capable of blocking Tim-3 signal pathway prepared by using a genetic engineering technique, the preparation method thereof, and use of the protein medicament in the treatment of immunological diseases.

The Tim-3-Ig fusion protein of the invention is prepared by expressing the fusion protein of a human Tim-3 fragment and a human Ig fragment.

The human Ig fragment of the invention is selected from the Fc segment or part thereof of human IgG, IgM, IgE, IgA and the subtypes thereof, such as IgG1, IgG2, IgG3, IgG4, and preferably IgG1.

Further, it is preferred in the present invention that the fragment of the amino acid sequence of human Tim-3 and the fragment of the amino acid sequence of human IgG1 are fused. More preferably, the fragment of the amino acid sequence of human Tim-3 and the fragment of the amino acid sequence of human IgG1 are fused.

The amino acid sequence of the fusion protein of the invention prepared by fusing a human Tim-3 fragment and a human Ig fragment is set forth in SEQ ID NO.1.

A person skilled in the art can understand that the terms "human Ig fragment" and the "human Tim-3" of the invention also encompass mutated forms of the polypeptide having same or similar biological activities. The mutated forms comprise, but not limited to: several (preferably 1-10, more preferably 1-5, most preferably 1-3) amino acid deletions, insertions and/or substitutions in relative to the amino acid sequence of said polypeptide. Furthermore, said deletions or insertions (additions) can take place at the C-terminal and/or N-terminal (typically within 20, preferably within 10, more preferably within 5 amino acid deletions or insertions). It is known in the art that a substitution by an amino acid with close or similar performance generally will not change the functions of the protein. The list of conservative amino acid substitutions for providing similar functions is well known in the art. The following 5 groups respectively comprise amino acids that can conservatively substitute each other: Aliphatic: glycine (G), alanine (A), valine (V), leucine (L), isoleucine (I); Aromatic: phenylalanine (F), tyrosine (Y), tryptophane (W); Sulphur-containing: methionine (M), cysteine (C); Alkaline: arginine (R), lysine (K), histidine (H); Acidic: aspartic acid (D), glutamic acid (E), asparagine (N), glutamine (Q). Furthermore, the terms also encompass fragment or derivative of T-cell immunoglobulin mucin, preferably that the fragment or derivative keeps the required biological activities of the protein.

The Tim-3 fragment and the Ig fragment is fused via a linking sequence therebetween.

The Ig sequence of the Tim-3-Ig fusion protein is connected via a linker (i.e. a linking peptide) to the Tim-3 fragment. The linker can be selected from many amino acids, such as alanine (Ala), glycine (Gly) and serine (Ser), or a combination of other amino acids, e.g. a combination of a series of glycines and serines, with the length being about 10-15 amino acids. The optimal length and amino acid composition of the linking peptide depend on the routine experiment requirements.

The DNA sequence of the Tim-3-Ig fusion protein of the invention is set forth in SEQ ID NO. 2.

It should be understood that, a person skilled in the art can synthesize a corresponding nucleotide sequence based on codon degeneracy and expression bias in different species. These variations are also encompassed in the scope of the invention.

The construction technique for a fusion protein is based on a molecular cloning method, and the specific experiment methods may refer to laboratory manuals like "Molecular Cloning" second version and third version.

PCR synthesis method is used to clone the DNA sequence encoding the above fusion protein into a vector. The vector for expressing the fusion protein can be a plasmid routinely used in molecular biology. A signal peptide sequence can be added to the N-terminal of the fusion protein, so as to assure the secretion of the protein from the cell. The sequence of vector comprises a promoter for driving the gene expression, starting and stop signal for protein translation, and PolyA sequence. The vector also contains an antibiotic resistance gene which allows the propagation of the plasmid in bacteria. Furthermore, the vector also comprises an eucaryotic cell selective gene for selecting a cell strain with stable transfection.

After finishing the construction of the plasmid, the DNA sequence of the fusion protein is verified by sequencing. The plasmid DNA is then used to transfect the cell, so as to express the corresponding protein. There are many expression systems for expressing these fusion proteins, including, but not limited to, mammal cells, bacteria, yeast, insect cells etc.

A protein expressed from mammal cells will have glycosylation modifications, and thus mammal cells are optimal for expressing the Tim-3-Ig fusion protein. There are many kinds of mammal cells that can be used for massive expression of a protein, including but not limited to, Chinese hamster ovary (CHO) cells, Hela cells, baby hamster kidney (BHK) cells, monkey-kidney cells (COS), human hepatocellular carcinoma cells (e.g. Hep G2), and many other cell lines.

The plasmid encoding the polypeptide can be introduced into a cell via transfection. There are many methods for cell transfection, including but not limited to: electroporation, liposome mediation, calcium mediation etc.

Besides mammale cells, other expression systems can also be used for the expression of these fusion proteins, e.g. bacteria, yeast, insect cells etc., and they are also encompassed in the scope of the cells that can be used in the invention. The protein yield of these expression systems may be higher than mammal cells, but the protein produced by such expression systems generally will lack glycosylation or the glyco-chain formed will be different to the mammal cells.

After the protein expression, enzyme-linked immunosorbent assay (ELISA) or other methods can be used to measure the concentration of the fusion protein in the cell culture. Since these fusion proteins have Ig fragment, and protein A or protein G affinity chramatography can be used for preliminary extraction of the expressed fusion protein.

The role of the Tim-3-Ig fusion protein of the invention is to competitively block the combination of Tim-3 and its ligand (Gal-9), so as to allow the immunocytes including T-cells, innate immunocytes such as macrophage etc. to be maintained in an activated state. The Tim-3-Ig fusion protein can be injected into the body of a patient as a purified recombinant protein. The DNA sequence encoding the fusion protein can be inserted into a proper vector, and is expressed in the body of a patient for gene therapy or cell therapy. Therefore, the fusion protein used in the method of the invention may have many different forms, not only including the protein per se, but also including the DNA encoding the fusion protein.

The present invention is also related to a pharmaceutical composition containing the fusion protein. The composition can contain a pharmaceutically acceptable carrier. The pharmaceutical composition can be various forms, including preferably injection, including aqueous and lyophilized injections. The pharmaceutical composition can be prepared according to conventional techniques in pharmacy, comprising mixing the pharmaceutical active ingredient, the polypeptide of the invention with the pharmaceutical carrier, and making the desired preparation according to techniques in pharmacy.

The present invention discloses a preparation containing the Tim-3-Ig fusion protein, which consists of the Tim-3-Ig fusion protein, a protectant, a buffer, a surfactant, and an isotonic regulator.

In one embodiment of the Tim-3-Ig fusion protein preparation, the content of the each component is as follows: the Tim-3-Ig fusion protein 10-40 mg/ml, the protectant 10-100 mg/ml, the buffer 3-10 mmol, the surfactant 0.05-0.2 mg/ml, and the isotonic regulator 2-9 mg/ml.

In one embodiment of the Tim-3-Ig fusion protein preparation, the protectant is disaccharide, trehalose, mannitol, glycine.

In one embodiment of the Tim-3-Ig fusion protein preparation, the buffer is sodium phosphate.

In one embodiment of the Tim-3-Ig fusion protein preparation, the surfactant is Tween-20.

In one embodiment of the Tim-3-Ig fusion protein preparation, the isotonic regulator is sodium chloride.

In one embodiment of the Tim-3-Ig fusion protein preparation, the content of the Tim-3-Ig fusion protein is 20 mg/ml, the content of the protectant is 37 mg/ml, the content of the buffer is 4.55 mmol, the content of the surfactant is 0.1 mg/ml, and the content of the isotonic regulator is 4 mg/ml.

DETAILED DESCRIPTION OF THE INVENTION

The below Examples are exemplary, they are only used for illustrating the invention, and should not be construed as a limitation of the invention. It should be indicated that, without departing the principle of the invention, a person skilled in the art can make several modifications, which also fall within the protection scope of the invention.

Example 1

Construction of an Expression Vector Containing the Fusion Protein

Experiment Materials: T4 DNA ligase; vector pcDNA3.1; competent bacteria JM109; plasmid extraction reagents; PCR reagents.

Methods and Results: Based on the sequences of human Tim-3 gene fragment and human IgG1 gene fragment disclosed in Genebank, human Tim-3-Ig gene containing a proper linking sequence was prepared via artificial synthesis. The human Tim-3-Ig gene was mixed with a vector by a proper ratio in T4 DNA ligase buffer, 0.5 U of T4 DNA ligase was added, and ligation was performed at 16° C. overnight. 10 µL of the ligation liquid was taken, added into 200 µL of competent bacteria JM109 and mixed gently. The mixture was subjected to ice bath for 30 min and 42° C. water bath for heat shock for 90 seconds, and then rapidly moved into ice bath for 2 min. 800 µL of LB medium was added to the mixture, and it was placed on a 37° C. constant temperature shaker with a shaking rate of 150 r/min for 45 min After 4000 r/min centrifugation for 1 min, 800 µL supernatant was discarded, and the pellet was taken and spread on a solid LB plate containing Amp (final concentration 100 µg/mL) The plate was placed upside-down in a 37° C. oven for 12-18 h. Single clones were picked from the plate and inoculated in a LB medium containing ampicillin (100 g/mL) The LB medium was placed on a 37° C. constant temperature shaker with a shaking rate of 170 r/min for overnight 3 mL of bacterial liquids were respectively taken and added into 15 mL Eppendorf tubes, which were centrifuged at 10000 r/min for 1 min, and the supernatant was discarded. Using a plasmid extraction kit, the bacteria pellet was resuspended in 100 µL Solution I, then 200 µL of freshly prepared Solution II was added, and it was gently reversed upside-down for several times until the liquid became clear. Subsequently, 150 µL of Solution III was added, and the liquid was gently reversed upside-down for several times until it was evenly mixed (a great deal of white flocculent precipitate appeared). After centrifugation at 4° C. and 12000 r/min for 5 min, the supernatant was taken and added into another Eppendorf tube, and equal volume of Tris-HCl saturated phenol was added. After thorough shaking and centrifugation at 12000 r/min for 5 min, the upper aqueous phase was transferred to a new tube. 500 µL of chloroform was then added, and the extraction was performed once again. Subsequently, the upper aqueous phase was carefully taken, and transferred into a new tube. 2 times of volume of absolute alcohol was added to the tube, mixed evenly, and placed at −20° C. for 3 h. After centrifugation at 4° C. and 12000 r/min for 10 min, the supernatant was discarded, and the pellet was washed with 70% alcohol twice, and then dried at room temperature for 20 min. The pellet was reconstituted with 40 µL sterile double distilled water, and then PCR identification and DNA sequencing analysis were performed. The results indicated that human Tim-3-Ig gene was successfully cloned into the expression vector pcDNA3.1, and the vector plasmid containing the target gene was named as pcDNA3.1-Tim-3-Ig (The sequence of Tim-3-Ig gene can be seen in SEQ ID NO.2).

Example 2

The Expression of Fusion Protein and Western Blot Assay

1. Experiment Materials:
Protein lysate; SDS-PAGE reagents; Tim-3 antibody (Abcam Company); NC film; Chinese hamster ovary cell (CHO cell); Protein A Sepharose CL 4B column (Beijing Vector Gene Technology co. Ltd.); 20% fetal bovine serum (Beijing YuanHeng ShengMa Biology Technology Research Institute); serum-free RPMI 1640 (Gibco Company).

2. Methods and Results:
1) The expression of the fusion protein: the recombinant plasmid pcDNA3.1-Tim-3-Ig prepared in the Example was transfected into CHO cells, which were cultured for several days, and then the supernatant was collected. 1 mL of 0.1 mol/L phosphate buffer (pH8.0) was added to the supernatant, and the pH was adjusted to 9.0 with 1 mol/L TRIS-HCL. The cell supernatant was loaded into a Protein A Sepharose CL 4B protein column (well equilibrated with pH8.0, 0.1 mol/L phosphate buffer), and the column was washed with the above buffer until no contaminant protein can be detected in the elute. Citrate buffer (pH3.0) was used for elution, and the elute was collected and immediately neutralized using 1 mol/L TRIS-HCL buffer (pH 8.5), and then dialyzed using 0.01 mol/L PBS (pH7.2) for 72 h. Product was taken to measure OD260 and OD280 in a UV-spectrophotometer, so as to calculate the content of the protein; the product was lyophilized and then stored at −20° C.

2) The Western Blot assay of the fusion protein: the product of the Tim-3-Ig fusion protein was collected for measuring protein concentration. SDS-PAGE gel was prepared, and then electrophoresis, membrane transfer, and blocking were conducted. Anti-human Tim-3 antibody was used for primary antibody incubation, secondary antibody incubation, and protein assay. The control protein in the experiment was Ig.

Figure 1:
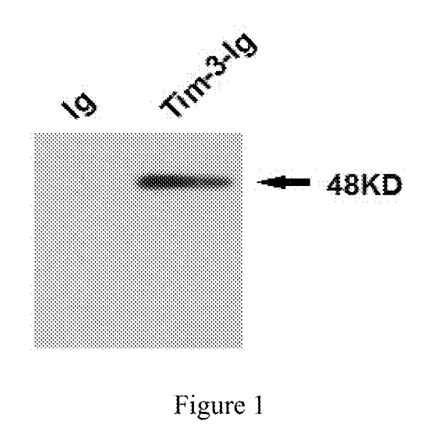
FIG. 1: Western Blot result of the human Tim-3-Ig fusion protein.

As shown in FIG. 1, Tim-3-Ig fusion protein can be specifically recognized by the anti-human Tim-3 antibody.

Example 3

ELISA Assay for the Binding Activity of the Fusion Protein

Experiment controls: negative control (merely containing the Ig of the invention), Control 1 (referred to as D1 protein with the sequence of SEQ ID NO.3), Control 2 (referred to as D2 protein with the sequence of SEQ ID NO.4), Control 3 (referred to as D3 protein with the sequence of SEQ ID NO.5), and Control 4 (referred to as D4 protein with the sequence of SEQ ID NO.6).

Methods and Results: after the fusion protein was prepared, binding trials were used in the invention to measure the binding activity between the Tim-3-Ig fusion protein and Gal-9. Negative control, Control 1, Control 2, Control 3, and Control 4 were also used. Specific procedures were as follows:

1) Gal-9 protein coating: Gal-9 protein with the concentration of 1-10 μg/ml in buffer was used to coat the wells of a PVC microtiter plate, and an adhesive plastic sheet was used to cover the microtiter plate. The plate was incubated at 4° C. overnight. The coating solution was discarded, and the microtiter plate was washed twice by adding 200 μl PBS into the wells each time and gently shaking the microtiter plate;

2) Blocking and loading: 200 μl blocking buffer (5% skimmed milk powder/PBS) was added to each well, so as to block and coat the remaining protein binding sites in the wells, and an adhesive plastic sheet was used to cover the microtiter plate. The plate was incubated at room temperature for at least 1-2 h. 100 μl of properly diluted Tim-3-Ig fusion protein or control protein was added to each well, and incubated at 37° C. for 90 min;

3) Incubation with anti-Tim-3 antibody: 100 μl of diluted anti-Tim-3 antibody was added into each well, and an adhesive plastic sheet was used to cover the microtiter plate. The plate was incubated at room temperature for 2 h, and the microtiter plate was washed using PBS for four times. 100 μl secondary antibody was added, which had been diluted to optimal concentration in the blocking buffer prior to use, and an adhesive plastic sheet was used to cover the microtiter plate. The plate was incubated at room temperature for 1-2 h, and then washed by PBS for four times; and 4) Detection: 100 μl substrate was added to each well and developed for 30 min. The data were read immediately at 405-410 nm.

The ELISA results showed that, as compared to the controls, the Tim-3-Ig fusion protein of the invention had better binding effects with Gal-9.

Example 4

The Blocking Activity of Human Tim-3-Ig Fusion Protein on Human Mononuclear Cell Line THP-1

Figure 2:
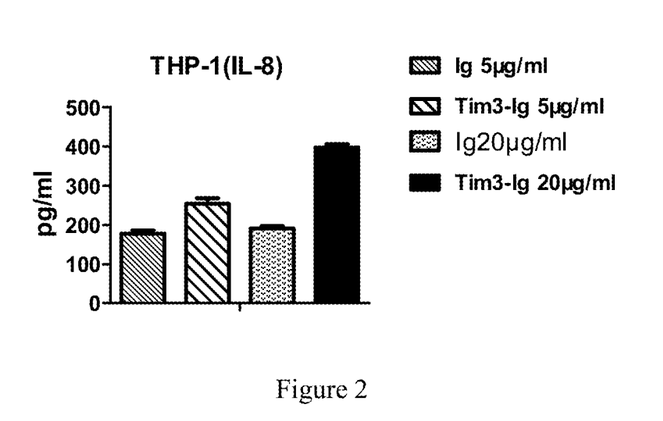
FIG. 2: The blocking activity of the human Tim-3-Ig fusion protein on human mononuclear cell line THP-1.

Tim-3-Ig fusion protein (with the concentration of 5 μg/ml and 20 μg/ml, respectively) and the negative control protein Ig (with the concentration of 5 μg/ml and 20 μg/ml, respectively) were co-cultured with human mononuclear cell THP-1, respectively. The secretion level of IL-8 in the supernatant of each group was detected after 48 h. As shown in FIG. 2, the Tim-3-Ig fusion protein can up-regulate the expression level of IL-8 in a dosage-dependent way.

Example 5

The Blocking Activity of Human Tim-3-Ig Fusion Protein on Human Macrophage Cell Line U937

Figure 3:
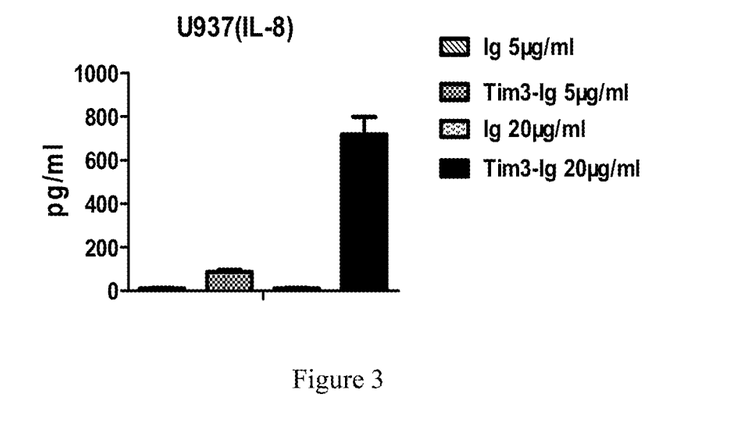
FIG. 3: The blocking activity of the human Tim-3-Ig fusion protein on human macrophage cell line U937.

Tim-3-Ig fusion protein (with the concentration of 5 μg/ml and 20 μg/ml, respectively) and the negative control protein Ig (with the concentration of 5 μg/ml and 20 μg/ml, respectively) were co-cultured with human macrophage U937, respectively. The secretion level of IL-8 in the supernatant of each group was detected after 48 h. As shown in FIG. 3, the Tim-3-Ig fusion protein can up-regulate the expression level of IL-8 in a dosage-dependent way.

Example 6

Figure 4:
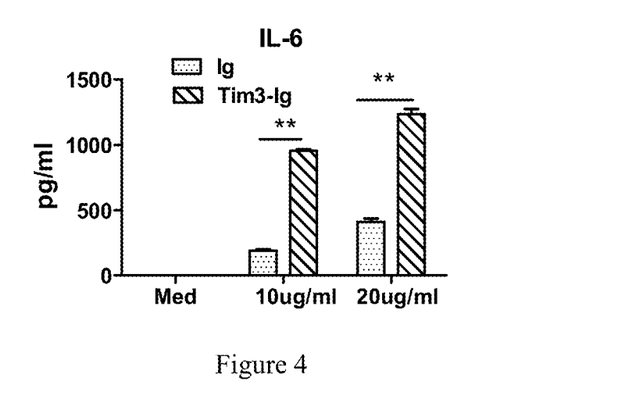
FIG. 4: The blocking activity of the human Tim-3-Ig fusion protein on human peripheral blood.

The Blocking Activity of Human Tim-3-Ig Fusion Protein on Human Peripheral Blood Isolated human peripheral blood (PBMC) was co-cultured with Tim-3-Ig (with the concentration of 10 μg/ml and 20 μg/ml, respectively), negative control protein Ig (with the concentration of 10 μg/ml and 20 μg/ml, respectively), and blank control, respectively. CD3 and CD28 were also used to stimulate cell proliferation. The supernatant was collected, and the expression of cytokine IL-6 was measured after 48 h. As shown in FIG. 4, the Tim-3-Ig fusion protein can significantly enhance the expression of IL-6 in PBMC.

Example 7

Figure 5:
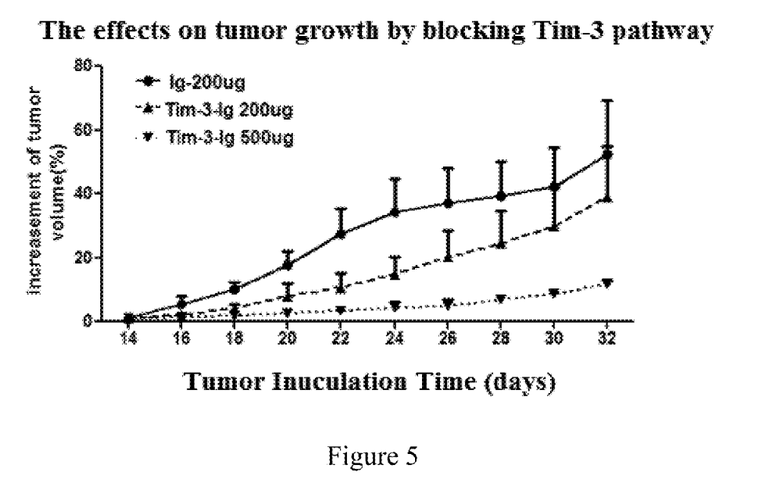
FIG. 5: The inhibiting effect of the human Tim-3-Ig fusion protein on the growth of the tumor in tumor bearing mice.
Figure 6:
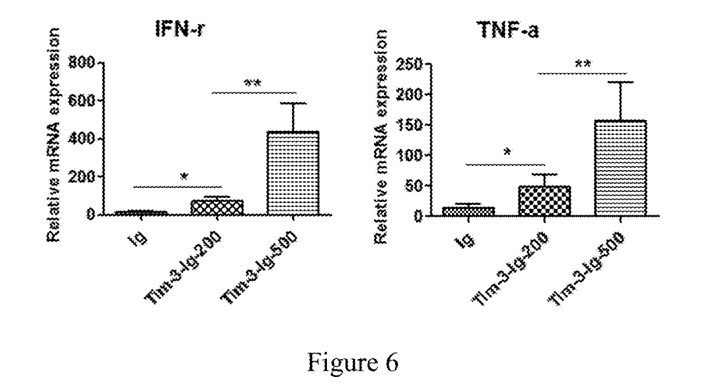
FIG. 6: The influence of the human Tim-3-Ig fusion protein on the immunological functions in tumor bearing mice.

The Effects of Human Tim-3-Ig Fusion Protein on the Growth of Tumor in Tumor Bearing Mice CT-26 tumor cells were first inoculated into the backside of Balb/C mice, and different dosages (200 μg and 500 μg) of Tim-3-Ig protein or the control protein Ig (200 μg) was simultaneously inoculated. Two weeks later, the changes in the size of tumor were monitored, and the size of tumor was measured on day 14, 16, 18, 20, 22, 24, 26, 28, 30, and 32, respectively. The results were shown in FIG. 5. As compared to the control, Tim3-Ig fusion protein can significantly inhibit the growth of tumor, and the inhibition effect of the Tim3-Ig fusion protein was dosage-dependent.

Example 8

The Effects of Human Tim-3-Ig Fusion Protein on the Immunological Functions in Tumor Bearing Mice In Example 7, spleen cells of the mice were collected at 38 days after the treatment of the Tim-3-Ig on tumor bearing mice. PCR method was used to detect the expressions of the cytokines IFN-γ and TNF-α in each group. The results were shown in FIG. 5. As compared to the control, Tim3-Ig fusion protein treatment can significantly increase the expression of immuno-cytokine, and the treatment of the Tim3-Ig fusion protein was dosage-dependent.

Example 9

The present invention further provides a preparation containing Tim-3-Ig fusion protein.

Formulation: Tim-3-Ig fusion protein 20 mg/ml; sucrose 37 mg/ml; sodium phosphate 0.35 mg/ml; Tween-20 0.1 mg/ml; sodium chloride 4 mg/ml.

The stock solution of the Tim-3-Ig fusion protein was obtained, and the concentration of Tim-3-Ig fusion protein should be higher than 20 mg/ml.

Formulation preparation: the required amounts of sucrose and Tween-20 (final concentration as 37 mg/ml and 0.1 mg/ml respectively) were calculated based on the volume of the stock solution, and then added into the stock solution. The concentrations of all the components in the solution were adjusted in accordance to the formulation, so as to obtain semi-finished products. The semi-finished products were sterilely divided into cillin bottles, which were capped with rubber plugs, lyophilized, and then capped with aluminum-plastic covers, so as to obtain the final products.

In the above Examples, in vitro experimental results indicated that Tim-3-Ig fusion protein can enhance the activation of human mononuclear macrophage (U937, THP-1) and human peripheral blood mononuclear cell (PBMC); and in vivo experimental results indicated that the fusion protein can enhance the immunological responses in tumor bearing mice by blocking the immunosuppressive functions of Tim-3, and inhibit the growth of tumor in a dosage-dependent way.

The invention claimed is:

1. A Tim-3-Ig fusion protein, wherein the amino acid sequence of the Tim-3-Ig fusion protein is set forth in SEQ ID NO: 1.

2. The Tim-3-Ig fusion protein according to claim 1, wherein the nucleotide sequence encoding the Tim-3-Ig fusion protein is set forth in SEQ ID NO: 2.

3. A vector comprising the nucleotide sequence which encodes a Tim-3-Ig fusion protein and is set forth in SEQ ID NO: 2.

4. A pharmaceutical composition for increasing the expression of immunocytokines and/or inhibiting a tumor, comprising the Tim-3-Ig fusion protein according to claim 1 and a pharmaceutically acceptable carrier.

5. The pharmaceutical composition according to claim 4, comprising 10-40 mg/ml of the Tim-3-Ig fusion protein, 10-100 mg/ml of a protectant, 3-10 mmol of a buffer, 0.05-0.2 mg/ml of a surfactant, and 2-9 mg/ml of an isotonic regulator.

* * * * *